US010161949B2

(12) United States Patent
Schacher et al.

(10) Patent No.: US 10,161,949 B2
(45) Date of Patent: Dec. 25, 2018

(54) METHOD AND DEVICE FOR TRANSFERRING SAMPLE TUBES BETWEEN A LABORATORY AUTOMATION SYSTEM AND A SAMPLE ARCHIVING SYSTEM

(71) Applicant: Roche Diagnostics Operations, Inc., Indianapolis, IN (US)

(72) Inventors: Gottlieb Schacher, Kriens (CH); Beat Jaeggi, Lucerne (CH); Harald Ferihumer, Hitzkirch (CH); Patrik Imfeld, Emmenbruecke (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/404,683

(22) Filed: Jan. 12, 2017

(65) Prior Publication Data

US 2017/0212141 A1    Jul. 27, 2017

(30) Foreign Application Priority Data

Jan. 22, 2016  (EP) .................................. 16152357

(51) Int. Cl.
*G01N 35/04* (2006.01)
*B65G 43/10* (2006.01)
*G01N 35/00* (2006.01)

(52) U.S. Cl.
CPC ........ *G01N 35/04* (2013.01); *G01N 35/00732* (2013.01); *G01N 2035/00752* (2013.01);
(Continued)

(58) Field of Classification Search
CPC ... G01N 35/04; G01N 35/00732; B65G 43/10
(Continued)

(56) References Cited

U.S. PATENT DOCUMENTS 1,892,206 A   12/1932  Dietz
2,417,823 A    3/1947  Hodson et al.
(Continued)

FOREIGN PATENT DOCUMENTS

CN    2646101 Y   10/2004
CN  201133910 Y   10/2008
(Continued)

OTHER PUBLICATIONS

US 2017/0350912 A1, Maetzler et al., Dec. 7 (Year: 2017).*
Extended European Search Report dated Jul. 14, 2016, in Application No. 16152357.6, 8 pages.

*Primary Examiner* — Douglas A Hess
(74) *Attorney, Agent, or Firm* — Roche Diagnostics Operations, Inc.

(57) ABSTRACT

A method and a device for transferring tubes between a laboratory automation system and a sample archiving system are presented. When transferring a tube from the laboratory automation system to the sample archiving system, a tube carrier carrying a tube is conveyed to a first take-over module via a first conveyor. At the first take-over module, the tube is removed from the tube carrier and the empty tube carrier is conveyed away from the first take-over module via a second conveyor. When transferring a tube from the sample archiving system to the laboratory automation system, an empty tube carrier is conveyed to a second take-over module via a third conveyor. At the second take-over module, at least one tube is inserted into the tube carrier and the tube carrier carrying the at least one tube is conveyed away from the second take-over module via a fourth conveyor.

18 Claims, 2 Drawing Sheets

(52) U.S. Cl.
CPC ............... *G01N 2035/041* (2013.01); *G01N 2035/0406* (2013.01); *G01N 2035/0429* (2013.01); *G01N 2035/0441* (2013.01); *G01N 2035/0455* (2013.01); *G01N 2035/0462* (2013.01); *G01N 2035/0465* (2013.01); *G01N 2035/0467* (2013.01); *G01N 2035/0472* (2013.01)

(58) Field of Classification Search
USPC .................. 198/407, 441, 469.1, 575, 580
See application file for complete search history.

(56) References Cited

U.S. PATENT DOCUMENTS

| | | | |
|---|---|---|---|
| 2,628,708 | A | 2/1953 | Wahl et al. |
| 3,036,624 | A | 5/1962 | Carter |
| 3,190,466 | A | 6/1965 | Hostetler |
| 4,596,107 | A * | 6/1986 | Pfleger, Sr. .......... B07C 5/3408 198/370.03 |
| 5,078,257 | A * | 1/1992 | Carter, Jr. ............ B23P 21/004 198/346.2 |
| 5,297,668 | A | 3/1994 | Zink |
| 5,699,891 | A | 12/1997 | Gosdowski et al. |
| 5,765,675 | A | 6/1998 | Draghetti et al. |
| 5,800,780 | A | 9/1998 | Markin |
| 5,819,508 | A | 10/1998 | Kraft et al. |
| 6,053,303 | A | 4/2000 | Wang |
| 6,056,106 | A | 5/2000 | van Dyke, Jr. et al. |
| 6,520,313 | B1 | 2/2003 | Kaarakainen et al. |
| 6,871,566 | B2 | 3/2005 | Niwayama et al. |
| 7,152,504 | B2 | 12/2006 | Itoh |
| 8,083,994 | B2 * | 12/2011 | Neeper ............ G01N 35/00732 422/63 |
| 8,220,617 | B2 * | 7/2012 | Eberle ................. G01N 35/021 198/346.2 |
| 8,877,128 | B2 | 11/2014 | Fukugaki et al. |
| 8,973,736 | B2 * | 3/2015 | Johns .................. B01D 21/262 198/439 |
| 9,000,360 | B2 * | 4/2015 | DeWitte ................ G01N 30/06 250/288 |
| 9,063,103 | B2 * | 6/2015 | Pedrazzini ............. G01N 35/04 |
| 9,164,113 | B2 | 10/2015 | Friedman et al. |
| 9,248,982 | B2 * | 2/2016 | Eberhardt ............. G01N 35/04 |
| 9,267,957 | B2 * | 2/2016 | Haechler ............ G01N 35/025 |
| 9,321,621 | B2 * | 4/2016 | Kitano ................. B67C 7/0073 |
| 9,481,528 | B2 * | 11/2016 | Pedrazzini ............. G01N 35/04 |
| 9,527,233 | B2 * | 12/2016 | Winzinger ............. B29C 49/36 |
| 9,733,161 | B2 * | 8/2017 | Nagai ..................... G01N 1/28 |
| 9,910,054 | B2 * | 3/2018 | Johns ................ G01N 35/0099 |
| 2006/0245865 | A1 | 11/2006 | Babson |
| 2007/0112399 | A1 | 5/2007 | Baek |
| 2013/0233673 | A1 | 9/2013 | Itoh |
| 2013/0239527 | A1 | 9/2013 | Clarke et al. |
| 2014/0036276 | A1 | 2/2014 | Gross et al. |
| 2014/0342465 | A1 | 11/2014 | Haechler et al. |
| 2015/0177268 | A1 | 6/2015 | Reisch et al. |
| 2015/0233955 | A1 | 8/2015 | Nemoto et al. |
| 2017/0101272 | A1 | 4/2017 | Cherubini et al. |
| 2017/0212139 | A1 | 7/2017 | Jaeggi |
| 2017/0212140 | A1 | 7/2017 | Ferihumer et al. |

FOREIGN PATENT DOCUMENTS

| | | |
|---|---|---|
| CN | 101309581 A | 11/2008 |
| CN | 102602697 A | 7/2012 |
| CN | 204613223 U | 9/2015 |
| EP | 2485058 A1 | 8/2012 |
| EP | 2253960 B1 | 5/2013 |
| EP | 2887071 A1 | 6/2015 |
| GB | 797685 | 7/1958 |
| JP | H07-234228 A | 9/1995 |
| JP | 2004-223646 A | 8/2004 |
| WO | 1983/000393 A1 | 2/1983 |
| WO | 2011/138448 A1 | 11/2011 |
| WO | 2014002953 A1 | 1/2014 |
| WO | 2014/147877 A1 | 9/2014 |
| WO | 2015/059620 A1 | 4/2015 |

* cited by examiner

METHOD AND DEVICE FOR TRANSFERRING SAMPLE TUBES BETWEEN A LABORATORY AUTOMATION SYSTEM AND A SAMPLE ARCHIVING SYSTEM

CROSS-REFERENCE TO RELATED APPLICATIONS

This application claims priority to EP 16152357.6, filed Jan. 22, 2016, which is hereby incorporated by reference.

BACKGROUND

The present disclosure relates to a method and a device for transferring sample tubes between a laboratory automation system and a sample archiving system.

Samples, for example, blood, saliva, swab, urine and other specimens taken from the human body, can be processed in a laboratory automation system comprising a number of pre-analytical, analytical and/or post-analytical stations. It is generally known to provide sample tubes containing the samples. The sample tubes are also referred to as test tubes. For processing of the sample, the sample tubes are distributed to designated stations or operating positions of the laboratory automation system.

Several sample tubes can be placed in racks for a handling and for a distribution with the laboratory automation system. In an alternative system, sample tubes are placed in an upright or vertical position in so called pucks having a retaining area for retaining one single sample tube. The pucks are also referred to as single sample tube carriers.

For a archiving of the samples, it is known for example to freeze the samples or to take additional, or other measures, in order to preserve the sample for a later use.

Therefore, there is a need for a method and a device for transferring sample tubes between a laboratory automation system and a sample archiving system.

SUMMARY

According to the present disclosure, a method and a device for transferring sample tubes between a laboratory automation system and a sample archiving system are presented. The device can comprise an input module for transferring a sample tube from the laboratory automation system to the sample archiving system. The input module can comprise a first take-over module, a first conveyor line for conveying a sample tube carrier carrying at least one sample tube to the first take-over module, and a second conveyor line for conveying an empty sample tube carrier away from the first take-over module. The device can also comprise an output module for transferring a sample tube from the sample archiving system to the laboratory automation system. The output module can comprise a third conveyor line for conveying an empty sample tube carrier to a second take-over module, and a fourth conveyor line for conveying a sample tube carrier carrying at least one sample tube away from the second take-over module.

Accordingly, it is a feature of the embodiments of the present disclosure to provide for a method and a device for transferring sample tubes between a laboratory automation system and a sample archiving system. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
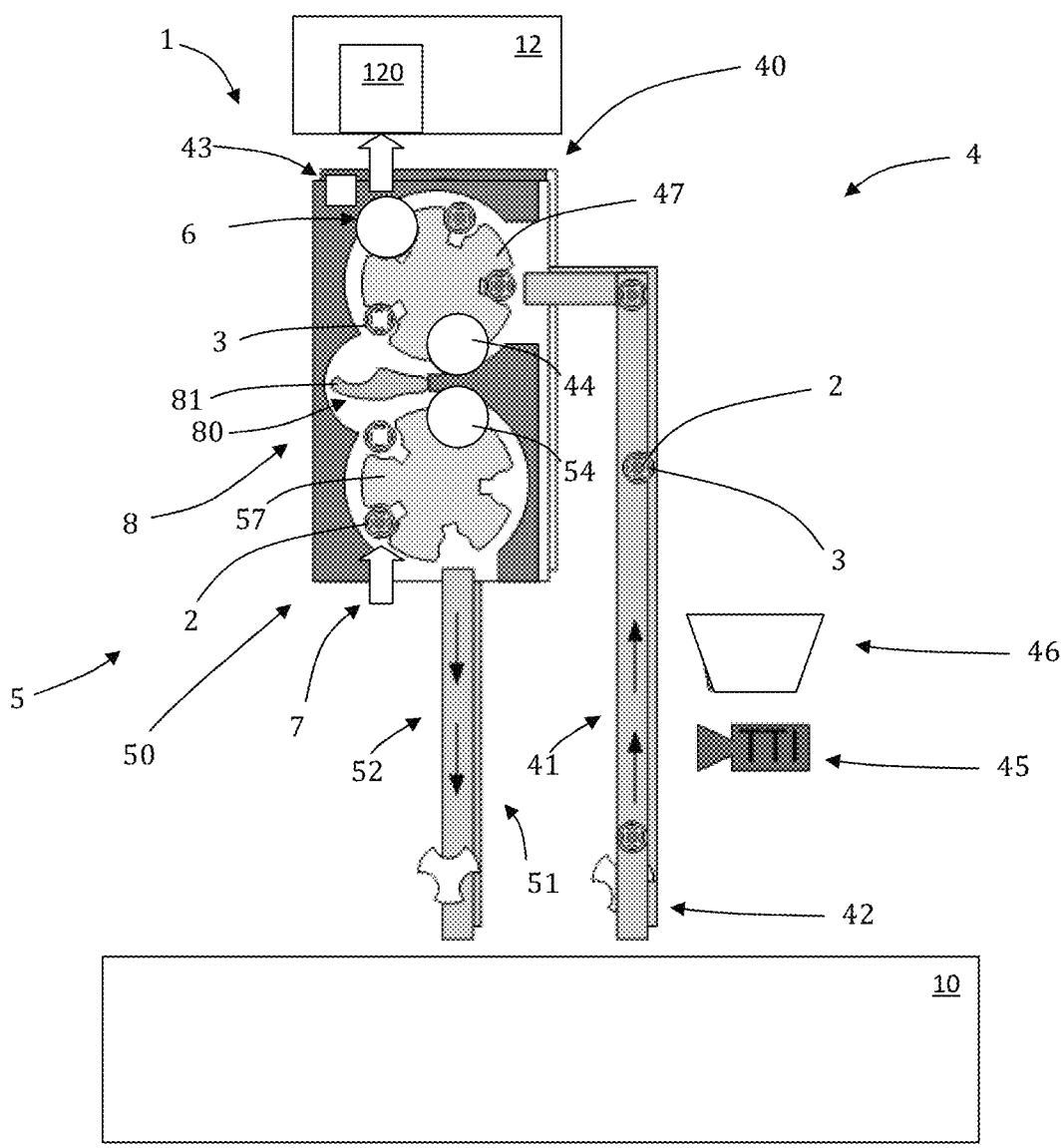
FIG. 1 illustrates a top view of a first embodiment of a device for transferring sample tubes between a laboratory automation system and a sample archiving system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for transferring sample tubes between a laboratory automation system and a sample archiving system is provided. When transferring a sample tube from the laboratory automation system to the sample archiving system, a sample tube carrier carrying at least one sample tube can be conveyed to a first take-over module via a first conveyor line. At the first take-over module, the at least one sample tube can be removed from the sample tube carrier and the empty sample tube carrier can be conveyed away from the first take-over module via a second conveyor line. When transferring a sample tube from the sample archiving system to the laboratory automation system, an empty sample tube carrier can be conveyed to a second take-over module via a third conveyor line. At the second take-over module, at least one sample tube can be inserted into the sample tube carrier and the sample tube carrier carrying the at least one sample tube can be conveyed away from the second take-over module via a fourth conveyor line.

Four independent conveyor lines can be provided allowing the operations of loading samples to the archiving systems and retrieving samples from the archiving system to be carried out independently. The term "conveyor line" may not be understood as being limited to devices conveying along a linear path. The conveyor line may comprise any kind of suitable conveyor device taken for example from the group comprising a screw conveyor, a carousel, a transfer belt, a two dimensional (2D) magnetic transport system or combinations thereof.

According to one embodiment, in the case of an irregularity of the sample archiving system, sample tube carriers carrying at least one sample tube can be transferred from the first conveyor line to the fourth conveyor line. In other words, in the case of a failure of the archiving system or any other irregularity, sample tube carriers carrying sample tubes can be transferred back to the laboratory automation system in order to avoid any damage to the sample or a loss of samples.

In one embodiment, prior to transferring sample tube carriers carrying at least one sample tube from the first conveyor line to the fourth conveyor line, the first conveyor line can be stopped while further operating the fourth conveyor line until the fourth conveyor line has sufficient capacity for receiving sample tube carriers from the first conveyor line. Thereby, any collision of sample tube carriers on the fourth line or conveying elements upstream, of the fourth line can be avoided.

In one embodiment, empty sample tube carriers and sample tube carriers carrying at least one sample tube can be conveyed at different conveying levels. Hence, temperature, air, pressure and other environmental conditions can be adapted to the needs for conveying carriers carrying sample tube carriers without increasing the overall costs of the system.

In one embodiment, in the case of different conveying levels, only empty sample tube carriers can be moved in the horizontal direction. In one embodiment, after the at least one sample tube is removed from the sample tube carrier, the empty sample tube carrier can be moved via a lifting device from the conveying level of the first conveyor line to the conveying level of the second conveyor line and/or before the at least one sample tube is inserted into the empty sample tube carrier, the empty sample tube carrier can be moved via a lifting device from the level of the third conveyor line to the level of the fourth conveyor line.

A device for transferring sample tubes between a laboratory automation system and a sample archiving system is provided. The device can comprise an input module for transferring a sample tube from the laboratory automation system to the sample archiving system. The input module can comprise a first take-over module, a first conveyor line for conveying a sample tube carrier carrying at least one sample tube to the first take-over module, and a second conveyor line for conveying an empty sample tube carrier away from the first take-over module. The device can also comprise an output module for transferring a sample tube from the sample archiving system to the laboratory automation system. The output module can comprise a third conveyor line for conveying an empty sample tube carrier to a second take-over module and a fourth conveyor line for conveying a sample tube carrier carrying at least one sample tube away from the second take-over module.

In one embodiment, the device can comprise a selectively operable transfer device arranged to be operated in case of an irregularity of the sample archiving system for transferring sample tube carriers carrying at least one sample tube from the first conveyor line to the fourth conveyor line. The transfer device can comprises a swivelably, or rotatably, arranged track switch. Hence, in a normal operation mode, the input module and the output module can be operated independently from each other. However, in case of an irregularity, for example, a failure of the archiving system, sample tube carriers conveyed by the input module towards the archiving system can be transferred back to the laboratory automation system via the output module.

In one embodiment, the conveyor lines of the device can be operable independently allowing the first conveyor line to be stopped while further operating the fourth conveyor line until the fourth conveyor line has sufficient capacity for receiving sample tube carriers from the first conveyor line, prior to transferring sample tube carriers carrying at least one sample tube from the first conveyor line to the fourth conveyor line.

In one embodiment, the device can have at least two different conveying levels. Empty sample tube carriers and sample tube carriers carrying at least one sample tube can be conveyed at different conveying levels. The conveying levels can each be adapted to the requirements of the items conveyed.

In one embodiment, the input module can comprise a first lifting device for moving the sample tube carriers from the conveying level of the first conveyor line to the conveying level of the second conveyor line. The lifting device may be arranged to transfer the carriers prior to an emptying. In some embodiments, the lifting device can be arranged for moving empty sample tube carriers from the conveying level of the first conveyor line to the conveying level of the second conveyor line. Hence, sample tubes may not be entering the conveying level for the empty sample tube carriers.

Likewise, in one embodiment, the output module can comprise a second lifting device for moving the sample tube carriers from the conveying level of the third conveyor line to the conveying level of the forth conveyor line. In some embodiments, the lifting device can be arranged for moving empty sample tube carriers from the conveying level of the third conveyor line to the conveying level of the fourth conveyor line.

In one embodiment, the input module can comprise at least one of a supervising device such as, for example, a camera, a recapping device, and an identification device such as, for example, a barcode reader. This can ensure that the sample tubes are securely closed and unambiguously identified prior to loading the sample tube into the sample archiving system. In other embodiments, the steps can be carried out at least party by the sample archiving system.

In one embodiment, at least one of the input module and the output module can comprise at least one carousel for conveying a sample tube carrier by rotation. The carousel can allow a precise positioning of singular sample tube carriers at defined positions along the periphery of the carousel. The carousel can be suitable for single sample tube carriers adapted for retaining exact one sample tube.

A laboratory automation system with a number of pre-analytical, analytical and/or post-analytical stations for carrying out the method for transferring sample tubes between a laboratory automation system and a sample archiving system described above with a device for transferring sample tubes between a laboratory automation system and a sample archiving system described above is presented Referring initially to FIG. 1, FIG. 1 shows a device 1 for transferring sample tubes 2 conveyed by a sample tube carrier 3 between a laboratory automation system 10 (schematically indicated by a block) and a sample archiving system 12 (schematically indicated by a block). In the embodiment shown, the sample tube carriers 3 can be single sample tube carriers. Only one sample tube 2 is retained in each carrier 3. However, the present disclosure is not limited to this type of carrier.

The device 1 can comprise an input module 4 for transferring a sample tube 2 from the laboratory automation system 10 to the sample archiving system 12 and an output module 5 for transferring a sample tube 2 from the sample archiving system 12 to the laboratory automation system 10.

The input module 4 can comprise a first take-over module 40, a first conveyor line 41 for conveying sample tube carriers 3 carrying sample tubes 2 to the first take-over module 40, and a second conveyor line 42 for conveying an empty sample tube carrier 3 away from the first take-over module 40. At the take-over module 40, the sample tube 2 can be presented to a suitable device 6 (schematically indicated by a circle and an arrow), in which device 6 can take the sample tube 2 from the sample tube carrier 3 and can supply the sample tube 2 to the sample archiving system 12. An identification device such as, for example, a barcode reader 43 can be provided adjacent to the device 6 for ensuring a correct archiving of the sample contained in the sample tube 2.

The two conveyor lines 41, 42 of the input module 4 can be operated independently. In other words, the first conveyor line 41 may be stopped, while continuing an operation of the second conveyor line 42. In the embodiment shown, the first conveyor line 41 and the second 42 can be arranged at different levels. In the embodiment shown, the first conveyor line 41 for conveying sample tube carriers 3 carrying a sample tube 2 can be placed above the second conveyor line 42. A height of the conveyor level for the second conveyor line 42 conveying only empty sample tube carriers 3 may be chosen smaller than that of the first conveyor line 41. The input module 4 can further comprise a first lifting device 44 arranged downstream of the device 6 taking the sample tubes 2 from the sample tube carriers 3 for moving the empty sample tube carriers 3 from the conveying level of the first conveyor line 41 to the conveying level of the second conveyor line 42, i.e. for lowering the empty sample tube carrier 3 in the embodiment shown.

In the embodiment shown, the input module 4 can further comprise a supervising device such as, for example, a camera 45 and a recapping device 46, which can be arranged along the first conveyor line 41.

The output module 5 can comprise a second take-over module 50, a third conveyor line 51 for conveying an empty sample tube carrier 3 to the second take-over module 50, and a fourth conveyor line 52 for conveying a sample tube carrier 3 carrying at least one sample tube 2 away from the second take-over module 50. At the second take-over module 50, the sample tube carrier 3 can be presented to a suitable device 7 (indicated by an arrow), in which the device 7 can insert at least one sample tube 2 taken from the sample archiving system 12 into the sample tube carrier 3.

In the embodiment shown, the third conveyor line 51 and the fourth 52 can be arranged at different levels. In the embodiment shown, the fourth conveyor line 52 for conveying sample tube carriers 3 carrying a sample tube 2 can be placed above the third conveyor line 51. The first conveyor line 41 and the fourth conveyor line 52 can be arranged at the same level. Likewise, the second conveyor line 42 and the third conveyor line 51 can be arranged at the same level. The output module 50 can further comprise a second lifting device 54 arranged upstream of the device 7 inserting the sample tubes 2 into the empty sample tube carriers 3 for moving the empty sample tube carriers 3 from the conveying level of the third conveyor line 51 to the conveying level of the fourth conveyor line 52, i.e. for lifting the empty sample tube carrier 3 in the embodiment shown.

The first take-over module 40 and the second take-over module 50 can each comprise an upper carousel 47, 57 and a lower carousel. Only the upper carousels 47, 57 of each module are visible. The upper carousels 47, 57 and the lower carousels of each take-over module 40, 50 in some embodiments can be driven to rotate independent of each other. In other embodiments, the upper carousels 47, 57 and the lower carousels of each take-over module 40, 50 can be coupled to rotate conjointly about a common axis of rotation.

In some embodiments, the archiving system 12 can be placed above the device 1. Further, the archiving system 12 can have a handover position 120. The handover position 120 of the archiving system, a handover position of the first take-over module 40, and a handover position of the second take-over module 50 can be aligned. Therefore, a single gripper device 6, 7 with two axis of motion may be sufficient for transferring sample tubes from the first take-over module 40 to the archiving system 12 and from the archiving system 12 to the take-over module 50.

In a normal operation mode, the input module 4 and the output module 5 can be operated independently. However, between the upper carousels 64, 74 a transfer device 8 can be provided, which can be arranged to be operated in case of an irregularity of the sample archiving system 12 for transferring sample tube carriers 3 carrying at least one sample tube 2 from the first conveyor line 41 to the fourth conveyor line 52. Hence, it can be avoided that sample tubes 2 not entering the archiving system remain stranded in the first take-over module 40 and/or are erroneously conveyed towards the second line 42 of the input module 4.

In the embodiment shown, the transfer device 8 can comprise a swivelably, or rotatably, arranged track switch 80 comprising one radially extending finger 81 for pushing the sample tube carrier 3 from the upper carousel 47 of the first take-over module 40 to the upper carousel 57 of the second take-over module 50.

In a normal operation mode, sample tube carriers 3 carrying a sample tube 2 can be conveyed via the first conveyor line 41 to the upper carousel 47 of the first take-over module 40 and by means of the upper carousel 47 into a position, in which the device 6 can take the sample tube 2 from the carrier 3 and can transfer it into the sample archiving system 12. The then empty sample tube carrier 3 can be transferred by the upper carousel 47 to the lifting device 44, then lowered by the lifting device 44 to a lower carousel or any other suitable conveying device for conveying the empty sample tube carrier 3 to the second conveyor line 42.

Empty sample tube carriers 3 can be conveyed via the third conveyor line 51 to the lower carousel of the second take-over module 50 or any other suitable conveyor device to the second lifting device 54 and lifted by the second lifting device 54 to the level of the upper carousel 57. By the upper carousel 57, the empty sample tube carriers 3 can be moved into a position, in which the device 7 can insert a sample tube 2 from the sample archiving system 12 into the sample tube carrier 3. The loaded sample tube carrier 3 can be transferred by the upper carousel 57 to the fourth conveyor line 52 and towards the laboratory automation system 10.

In case of an irregularity, for example in the case of a failure of the sample archiving system 12, the first line 41 can be stopped or decreased in speed. The upper carousel 57 of the second transfer module and/or the fourth line 52 can be cleared and the transfer device 8 can be operated to move sample tube carriers 3 carrying sample tubes 2 to the fourth line 52 and via the fourth line to the laboratory automation system 10.

Figure 2:
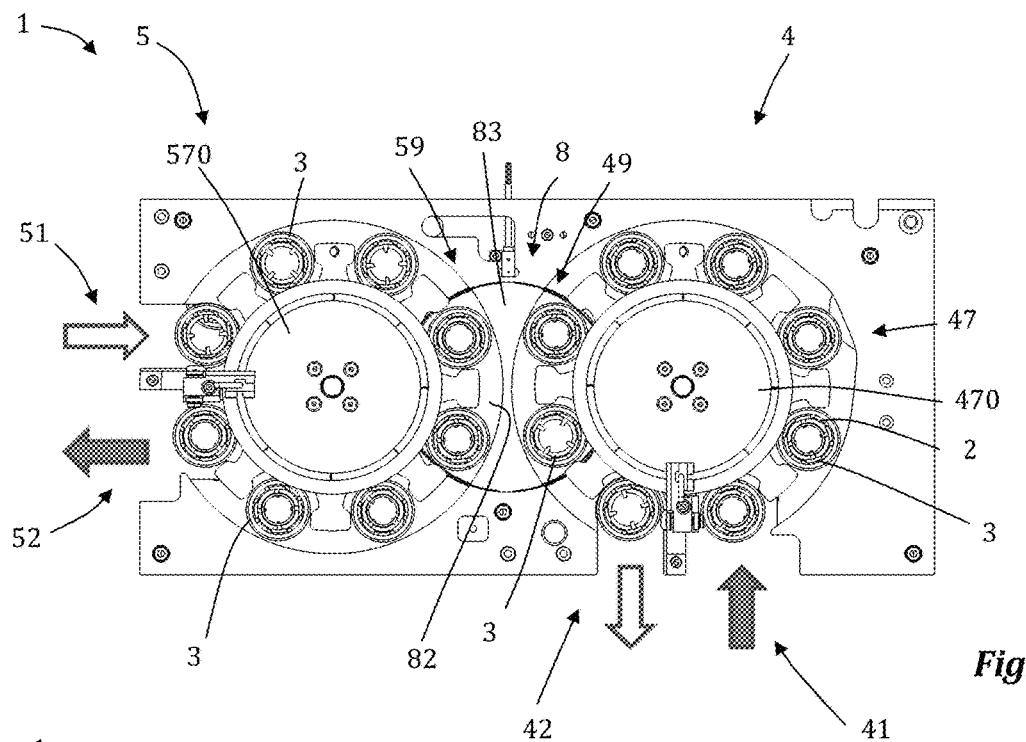
FIG. 2 illustrates a top view of a device similar to FIG. 1 during normal operation according to an embodiment of the present disclosure.
Figure 3:
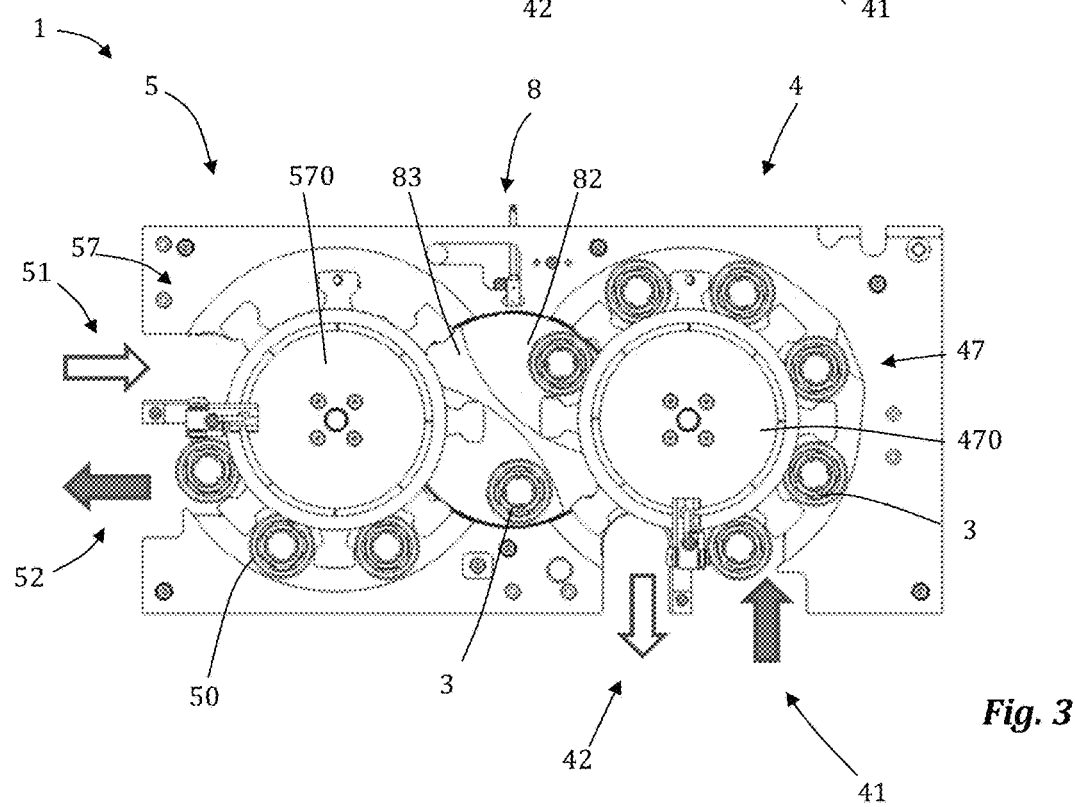
FIG. 3 illustrates a top view of the device of FIG. 2 during operation in case of irregularities according to an embodiment of the present disclosure.

FIGS. 2 and 3 show a top view of second embodiment of a device 1 similar to the device 1 shown in FIG. 1 with an input module 4 comprising a first carousel 47 with a disc 470 and an output module 5 comprising a second carousel 57 with a disc 570.

Sample tube carriers 3 carrying sample tubes 2 can be fed via a first conveyor line 41 to the carousel 47 and can be moved by the carousel 47 to a position 49. At the position 49, a device (not shown) can take the sample tube 2 from the sample tube carrier 3 and the empty sample tube carrier can be conveyed by the carousel 47 to the second conveyor line 42. Likewise, empty sample tube carriers 3 can be fed via a third conveyor line 51 to the carousel 57 and can be moved by the carousel 57 to a position 59. At the position 59, a device (not shown) can insert a sample tube 2 into the sample tube carrier 3 and the loaded sample tube carrier 3 can be conveyed by the carousel 57 to the fourth conveyor line 52.

A transfer device 8 comprising a rotary disc 82 and a separation wall 83 can be provided between the two carousels 47, 57. If required, the transfer device 8 can be driven to transfer sample tube carriers 4 from the first carousel 47 to the second carousel 57.

FIG. 3 shows an operation, wherein sample tube carriers 3 can be transferred from the first carousel 47 to the second carousel 57. For this purpose, the first carousel 47 can be stopped and the second carousel 57 can be completely unloaded or at least unloaded to have to a series of consecutive empty recesses arranged at a transfer area.

Next, the second carousel 57 can be stopped and the disc 82 of the transfer device 8 can be driven to rotate at least by 180°, wherein at first the transfer disc 82 can be driven to rotate together with the first carousel 47 and, after forwarding the first carousel 47 one step ahead, the transfer disc 82 can be driven to rotate by itself to move a sample tube carrier 3 from the first carousel 47 to the second carousel 57.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A method for transferring sample tubes between a laboratory automation system and a sample archiving system, the method comprising:
   when transferring a sample tube from the laboratory automation system to the sample archiving system, a sample tube carrier carrying at least one sample tube is conveyed to a first take-over module via a first conveyor line, at the first take-over module, the at least one sample tube is removed from the sample tube carrier, and the empty sample tube carrier is conveyed away from the first take-over module via a second conveyor line; and
   when transferring a sample tube from the sample archiving system to the laboratory automation system, an empty sample tube carrier is conveyed to a second take-over module via a third conveyor line, at the second take-over module, at least one sample tube is inserted into the sample tube carrier, and the sample tube carrier carrying the at least one sample tube is conveyed away from the second take-over module via a fourth conveyor line.

2. The method according to claim 1, wherein in the case of an irregularity of the sample archiving system, sample tube carriers carrying at least one sample tube are transferred from the first conveyor line to the fourth conveyor line.

3. The method according to claim 2, wherein prior to transferring sample tube carriers carrying at least one sample tube from the first conveyor line to the fourth conveyor line, the first conveyor line is stopped while further operating the fourth conveyor line until the fourth conveyor line has sufficient capacity for receiving sample tube carriers from the first conveyor line.

4. The method according to claim 1, wherein empty sample tube carriers and sample tube carriers carrying at least one sample tube are conveyed at different conveying levels.

5. The method according to claim 4, wherein after the at least one sample tube is removed from the sample tube carrier, the empty sample tube carrier is moved via a lifting device from the conveying level of the first conveyor line to the conveying level of the second conveyor line.

6. The method according to claim 4, wherein before the at least one sample tube is inserted into the empty sample tube carrier, the empty sample tube carrier is moved via a lifting device from the level of the third conveyor line to the level of the fourth conveyor line.

7. A device for transferring sample tubes between a laboratory automation system and a sample archiving system, the device comprising:
   an input module for transferring a sample tube from the laboratory automation system to the sample archiving system, the input module comprising,
      a first take-over module,
      a first conveyor line for conveying a sample tube carrier carrying at least one sample tube to the first take-over module, and
      a second conveyor line for conveying an empty sample tube carrier away from the first take-over module;
   an output module for transferring a sample tube from the sample archiving system to the laboratory automation system, the output module comprising,
      a third conveyor line for conveying an empty sample tube carrier to a second take-over module, and
      a fourth conveyor line for conveying a sample tube carrier carrying at least one sample tube away from the second take-over module; and
   a selectively operable transfer device arranged to be operated in the case of an irregularity of the sample archiving system for transferring sample tube carriers carrying at least one sample tube from the first conveyor line to the fourth conveyor line.

8. A laboratory automation system with a number of pre-analytical, analytical and/or post-analytical stations for carrying out the method of claim 1 with a device according to claim 7.

9. The device according to claim 7, wherein the transfer device comprises a swivelably, or rotatably, arranged track switch.

10. The device according to claim 7, wherein the conveyor lines are operable independently allowing the first conveyor line to be stopped while further operating the fourth conveyor line until the fourth conveyor line has sufficient capacity for receiving sample tube carriers from the first conveyor line, prior to transferring sample tube carriers carrying at least one sample tube from the first conveyor line to the fourth conveyor line.

11. The device according to claim 7, wherein the input module comprises at least one supervising device such as a camera, a recapping device, and an identification device.

12. The device according to claim 11, wherein the identification device is a barcode reader.

13. The device according to claim 7, wherein at least one of the input module and the output module comprises at least one carousel for conveying a sample tube carrier by rotation.

14. A device for transferring sample tubes between a laboratory automation system and a sample archiving system, the device comprising:
  an input module for transferring a sample tube from the laboratory automation system to the sample archiving system, the input module comprising,
    a first take-over module,
    a first conveyor line for conveying a sample tube carrier carrying at least one sample tube to the first take-over module, and
    a second conveyor line for conveying an empty sample tube carrier away from the first take-over module; and
  an output module for transferring a sample tube from the sample archiving system to the laboratory automation system, the output module comprising,
    a third conveyor line for conveying an empty sample tube carrier to a second take-over module, and
    a fourth conveyor line for conveying a sample tube carrier carrying at least one sample tube away from the second take-over module;
    wherein the device has at least two different conveying levels and wherein empty sample tube carriers and sample tube carriers carrying at least one sample tube are conveyed at different conveying levels.

15. The device according to claim 14, wherein the input module comprises a first lifting device for moving the sample tube carriers from the conveying level of the first conveyor line to the conveying level of the second conveyor line.

16. The device according to claim 15, wherein the first lifting device moves empty sample tube carriers from the conveying level of the first conveyor line to the conveying level of the second conveyor line.

17. The device according to claim 14, wherein the output module comprises a second lifting device for moving the sample tube carriers from the conveying level of the third conveyor line to the conveying level of the forth conveyor line.

18. The device according to claim 17, wherein the second lifting device moves empty sample tube carriers from the conveying level of the third conveyor line to the conveying level of the fourth conveyor line.

\* \* \* \* \*